(12) United States Patent
Bjorkling et al.

(10) Patent No.: US 8,053,446 B2
(45) Date of Patent: Nov. 8, 2011

(54) CYANOGUANIDINE COMPOUNDS

(75) Inventors: Fredrik Bjorkling, Helsingborg (SE); Heinz Wilhelm Dannacher, Skovlunde (DK)

(73) Assignee: Leo Pharma A/S, Ballerup (DK)

( * ) Notice: Subject to any disclaimer, the term of this patent is extended or adjusted under 35 U.S.C. 154(b) by 781 days.

(21) Appl. No.: 11/793,867

(22) PCT Filed: Dec. 20, 2005

(86) PCT No.: PCT/DK2005/000803
§ 371 (c)(1),
(2), (4) Date: May 23, 2008

(87) PCT Pub. No.: WO2006/066584
PCT Pub. Date: Jun. 29, 2006

(65) Prior Publication Data
US 2008/0312275 A1  Dec. 18, 2008

Related U.S. Application Data

(60) Provisional application No. 60/637,757, filed on Dec. 22, 2004.

(51) Int. Cl.
*C07D 401/12* (2006.01)
*A61K 31/44* (2006.01)
(52) U.S. Cl. ......... 514/313; 514/323; 546/162; 546/264
(58) Field of Classification Search ........................ None
See application file for complete search history.

(56) References Cited

U.S. PATENT DOCUMENTS

| | | |
|---|---|---|
| 5,696,140 A | 12/1997 | Bramm et al. |
| 5,919,816 A | 7/1999 | Hausheer et al. |
| 6,346,541 B1 | 2/2002 | Hunneche |
| 6,525,077 B2 | 2/2003 | Binderup et al. |
| 6,642,215 B2 | 11/2003 | Madsen et al. |
| 6,645,968 B2 | 11/2003 | Altenbach et al. |
| 7,129,043 B1 | 10/2006 | Boustany et al. |
| 7,253,193 B2 | 8/2007 | Binderup et al. |
| 7,304,066 B2 | 12/2007 | Bjorkling |
| 7,807,682 B2 | 10/2010 | Bjorkling |
| 2003/0045515 A1 | 3/2003 | Binderup et al. |
| 2006/0014804 A1 | 1/2006 | Binderup |
| 2007/0249676 A1 | 10/2007 | Binderup et al. |

FOREIGN PATENT DOCUMENTS

| | | | |
|---|---|---|---|
| EP | 0 660 823 B1 | | 8/1996 |
| WO | WO-94/06770 | | 3/1994 |
| WO | WO-98/54141 A1 | | 12/1998 |
| WO | WO-98/54142 A1 | | 12/1998 |
| WO | WO-98/54143 A1 | | 12/1998 |
| WO | WO-98/54144 | | 12/1998 |
| WO | WO-98/54145 A1 | | 12/1998 |
| WO | WO-00/61559 | | 10/2000 |
| WO | WO-00/61561 A1 | | 10/2000 |
| WO | WO-01/09096 A | | 2/2001 |
| WO | WO 01/09096 A | * | 2/2001 |
| WO | WO-02/42265 | | 5/2002 |
| WO | WO-02/62762 | | 8/2002 |
| WO | WO-02/094322 A2 | | 11/2002 |
| WO | WO 02/094813 A | * | 11/2002 |
| WO | WO-02/094813 A | | 11/2002 |
| WO | WO-03/097601 A1 | | 11/2003 |
| WO | WO-03/097602 A1 | | 11/2003 |

OTHER PUBLICATIONS

West, Anthony R., Solid State Chemistry and its Applications, Wiley, New York, 1988, pp. 358 & 365.*
Bodor et al., "Soft alkylating compounds as potential antitumor agents", Journal of Medicinal Chemistry, 1980, vol. 23, No. 5, pp. 566-569.
Boschi et al, "Nicorandil analogues containing No-Donor Furoxans and related furazans," Bioorganic & Medical Chemistry, vol. 8, pp. 1727-1732 (2000).
Chen Jianyong et al., "Synthesis of Potassium Channel Opener Pinacidil and its Analogues," Journal of China Pharmaceutical University, vol. 24, No. 4, 1993, pp. 202-204, SP002902627.
Davidsen et al., "N-(acyloxyalkyl) pyridinium salts as soluble prodrugs of a potent platelet activating factor antagonist," Journal of Medicinal Chemistry, Dec. 23, 1994, vol. 37, No. 26, pp. 4423-4429.
Hjarnaa et al., CHS 828, a Novel Pyridyl Cyanoguanidine with Potent Antitumor Activity in Vitro and in vivo, Cancer Research, 59, 5751-5757, Nov. 15, 1999.
Martinsson et al., "The Combination of the antitumoural pyridyl cyanoguanidine CHS 828 and etoposide in vitro—from cytotoxic synergy to complete inhibition of apoptosis," British journal of Pharmacology, vol. 137, pp. 568-573 (2002).
Moriguchi, et al. "Adaptive Least-Squares Method Applied to Structure-Activity Correlation of Hypotensive N-Alkyl-N"-cyano-N' pyridylguanidines." Journal of Medicinal Chemistry, vol. 23, No. 1, 20-26. 1980.
Olsen, L.S. et al., "Anticancer Agent CHS Suppresses Nuclear Facor-κB Activity in Cancer Cells through Downregulation of IKK Activity," Int. J. Cancer, vol. 111, pp. 198-205, 2004.
Sara Ekelund et al, "Early Stimulation of Acidification rate by Novel Cytotoxic Pyridyl Cyanoguanidines in Human Tumor Cells: Comparison with m-lodobenzylguanidine," Biochemical Pharmacology, vol. 60, pp. 839-849, (2000).
Schou, C. et al. "Novel Cyanoguanidines with Potent Oral Antitumour Activity," Bioorganic & Medicinal Chemistry Letters, vol. 7, No. 24, pp. 3095-3100, 1997.
Svensson, A. et al. "CHS 828 Inhibits Neuroblastoma Growth in Mice Alone and in Combination with Antiangiogenic Drugs," Pediatric Research, vol. 51, No. 5, 2002, pp. 607-611.
International Search Report issued for International Patent Application No. PCT/DK2005/000803, filed Dec. 20, 2005.

* cited by examiner

*Primary Examiner* — Zinna Northington Davis
(74) *Attorney, Agent, or Firm* — Wilmer Cutler Pickering Hale and Dorr LLP

(57) ABSTRACT

Novel pyridyl cyanoguanidine compounds of general formula I (I) wherein $R_1$, X, $R_2$ and $R_3$ are as defined herein, exhibit a high antiproliferative activity and may be used in the treatment of hyperproliferative and neo-plastic diseases.

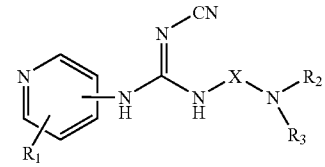

(I)

18 Claims, No Drawings

US 8,053,446 B2

CYANOGUANIDINE COMPOUNDS

FIELD OF INVENTION

The present invention relates to novel pyridyl cyanoguanidine compounds and their inclusion in pharmaceutical compositions, as well as their use in the manufacture of medicaments.

BACKGROUND OF THE INVENTION

Pyridyl cyanoguanidines such as pinacidil (N-1,2,2-trimethylpropyl-N'-cyano-N"-(4-pyridyl)guanidine) were originally discovered to be potassium channel openers and were consequently developed as antihypertensive agents. Replacement of the side chain of pinacidil by longer aryl-containing side chains caused a loss of the antihypertensive activity, but such compounds were, on the other hand, found to show antitumour activity on oral administration in a rat model carrying Yoshida ascites tumours.

Different classes of pyridyl cyanoguanidines with antiproliferative activity are disclosed in, for instance, EP 660 823, WO 98/54141, WO 98/54143, WO 98/54144, WO 98/54145, WO 00/61559 and WO 00/61561. The structure-activity relationships (SAR) of such compounds are discussed in C. Schou et al., Bioorganic and Medicinal Chemistry Letters 7(24), 1997, pp. 3095-3100, in which the antiproliferative effect of a number of pyridyl cyanoguanidines was tested in vitro on different human lung and breast cancer cell lines as well as on normal human fibroblasts.

P-J V Hjarnaa et al., Cancer Res. 59, 1999, pp. 5751-5757, report on the results of further testing of a specific cyanoguanidine compound, i.e. N-(6-(4-chlorophenoxy)hexyl)-N'-cyano-N"-(4-pyridyl)guanidine in in vitro and in vivo tests. The compound exhibited a potency in vitro which was comparable to that of the reference cytostatic agents daunorubicin and paclitaxel, while showing considerably less antiproliferative activity on normal human endothelial cells. In in vivo tests using nude mice transplanted with human tumour cells, the compound showed substantial antitumour activity, also against tumour cells that were resistant to conventional anticancer drugs such as paclitaxel.

A successful drug requires a subtle balance between factors such as activity, bio-availability, toxicity, level of side-affects, solubility, etc. which allows for improved cyanoguanidine based drugs.

SUMMARY OF THE INVENTION

The present inventors have found that novel pyridyl cyanoguanidine compounds comprising a heterocyclic radical substituted with a keto group at one carbon atom exhibit a surprisingly high anti-proliferative activity. Accordingly, the invention relates to compounds of formula I

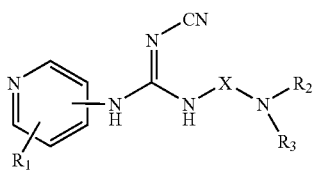

wherein
$R_1$ is one or more same or different substituents independently selected from the group consisting of hydrogen, halogen or a straight or branched, saturated or unsaturated $C_{1-6}$ hydrocarbon radical, optionally substituted with halogen, hydroxy, cyano, nitro, carboxy, alkoxy, alkoxycarbonyl, alkylcarbonyl, formyl, amino, aminoalkyl, aminocarbonyl, alkylcarbonylamino, sulfo, aminosulfonyl, alkylsulfonylamino, hydroxysulfonyloxy, dihydroxyphosphinoyloxy or phosphono;
X is a straight or branched, saturated or unsaturated $C_{1-12}$ hydrocarbon diradical, optionally substituted with halogen, hydroxy, cyano, nitro, carboxy, alkoxy, alkoxycarbonyl, alkylcarbonyl, formyl, amino, aminoalkyl, aminocarbonyl, alkylcarbonylamino, sulfo, aminosulfonyl, alkylsulfonylamino, hydroxysulfonyloxy, dihydroxyphosphinoyloxy or phosphono; and
$R_2$ and $R_3$ together with the nitrogen atom to which they are attached form a 5-12 membered mono- or bicyclic ring system optionally including one or more additional heteroatoms selected from the group consisting of nitrogen, sulphur or oxygen, said ring system being substituted with a group =O at one carbon atom thereof, and optionally substituted with one or more substituents selected from the group consisting of halogen, hydroxy, cyano, nitro, alkoxy, alkoxycarbonyl, alkylcarbonyl, formyl, aminoalkyl, a straight or branched, saturated or unsaturated $C_{1-6}$ hydrocarbon radical, optionally substituted with halogen, hydroxy, cyano, nitro, alkoxy, alkoxycarbonyl, alkylcarbonyl, formyl or aminoalkyl, or —C(=O)NR$_5$R$_6$, —NHC(=O)R$_5$, —NHC(=O)NR$_5$R$_6$, —NHC(=O)OR$_5$, —OC(=O)R$_5$ or

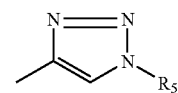

wherein $R_5$ and $R_6$ are the same or different and independently selected from the group consisting of hydrogen, $C_{1-6}$ alkyl optionally substituted with one or more halogen, hydroxy, cyano, nitro, amino, —NHC(=O)NR$_5$R$_6$, —NHC(=O)OR$_5$ or

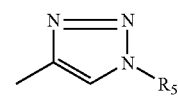

provided that $R_1$ is not attached to the nitrogen atom of the pyridyl ring;
or a pharmaceutically acceptable salt, solvate, hydrate, N-oxide or prodrug thereof.

The invention also relates to the use of a compound of formula I in therapy and to pharmaceutical compositions comprising a compound according to formula I.

The invention also relates to methods of treating or preventing diseases comprising administering to a patient an effective dose of a compound of formula I.

Furthermore, the invention relates to the use of compounds of formula I in the manufacture of medicaments for the treatment of hyperproliferative or neoplastic diseases.

DETAILED DESCRIPTION OF THE INVENTION

In the present context, the term "hydrocarbon radical" is intended to indicate a moiety comprising solely hydrogen and carbon, preferably comprising 1-18, e.g. 1-12, e.g. 1-6 carbon atoms. Examples of said hydrocarbon radical include methyl, ethyl, ethenyl, ethynyl, butyl, butenyl, butynyl, iso-butyl, tert.-butyl, hexyl, 1,3-di-methyl-hexyl, octyl, octenyl, nonyl, dodecyl, dodecenyl, etc. The radical or di-radical is obtained by removing one or two, respectively, hydrogen atoms from the hydrocarbon.

The term "halogen" is intended to indicate fluoro, chloro, bromo and iodo.

The term "pharmaceutically acceptable salt" is intended to indicate salts prepared by reacting compounds of formula I comprising acid or basic groups with suitable bases or acids, respectively. Examples of such acids are hydrochloric, hydrobromic, hydroiodic, sulfuric, nitric, acetic, phosphoric, lactic, meleic, phthalic, citric, propionic, benzoic, glutaric, gluconic, methanesulfonic, salicylic, succinic, tartaric, toluenesulfonic, sulfamic and fumaric acid. Examples of such bases are potassium hydroxide, sodium hydroxide, ammonia and amines.

The term "solvate" is intended to indicate a species formed by interaction between a compound, in casu a compound of formula I, and a solvent, e.g. alcohol, glycerol or water, wherein said species is in the solid form. When water is the solvent, the solvate is referred to a hydrate.

The term "N-oxide" is intended to indicate e.g. pyridyl N-oxide derivatives of the compounds of the invention. Such compounds may be prepared by oxidation of the pyridyl N by a suitable oxidising agent, e.g. 3-chloro-perbenzoic acid in an inert solvent, e.g. dichlormethan.

The term "alkyl" is intended to indicate mono-radicals obtained from alkanes, preferably comprising 1-8 carbon atoms, such as methyl, ethyl, propyl, butyl, isobutyl, tert.-butyl, pentyl, hexyl and cyclohexyl.

The term "alkoxy" is intended to indicate a radical of the formula —OR, wherein R is alkyl as indicated above.

The term "alkoxycarbonyl" is intended to indicate a radical of the formula —C(O)—OR, wherein R is alkyl as indicated above.

The term "alkylcarbonyl" is intended to indicate a radical of the formula —C(O)—R, wherein R is alkyl as indicated above.

The term "aminoalkyl" is intended to indicate a radical of the formula —R—NR'$_2$, wherein R is alkyl as indicated above, and each R' independently represent alkyl as indicated above or hydrogen.

The term "aminocarbonyl" is intended to indicate a radical of the formula —C(O)—NR'$_2$, wherein each R' independently represent alkyl as indicated above or hydrogen.

The term "alkylcarbonylamino" is intended to indicate a radical of the formula —N(R')—C(O)—R, wherein R and R' independently represent alkyl as defined above or hydrogen.

The term "aminosulfonyl" is intended to indicate a radical of the formula —S(O)$_2$—NR'$_2$, wherein each R' independently represent alkyl as indicated above or hydrogen.

The term "alkylsulfonylamino" is intended to indicate a radical of the formula —N(R')—S(O)$_2$—R, wherein R is alkyl as indicated above, and each R' independently represent alkyl as indicated above or hydrogen.

The term "amino" is intended to indicate a radical of the formula —NR'$_2$, wherein each R' independently represent alkyl as indicated above or hydrogen.

The term "prodrug" is intended to indicate a derivative of an active compound which does not, or does not necessarily, exhibit the physiological activity of the active compound, but which may be biologically activated, e.g. subjected to enzymatic cleavage such as hydrolysis in vivo so as to release the active compound on administration of the prodrug. The preparation of prodrugs of cyanoguanidine compounds similar to the compounds of the present invention is disclosed in International Patent Application Publication No. WO 02/43365. Thus, one may contemplate preparing prodrugs of the compound of formula I by attaching to the nitrogen atom of the pyridine ring a group of formula VI

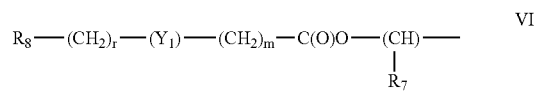

wherein
$R_7$ is hydrogen or straight, branched or cyclic alkyl, or an aromatic hydrocarbon radical;
$Y_1$ is O, OC(O), C(O)O or $NR_9$, wherein $R_9$ is hydrogen or $C_{1-4}$alkyl;
each of m and r are 0 or an integer from 1 to 4; and
$R_8$ is hydrogen; a straight, branched and/or cyclic hydrocarbon radical, optionally substituted with one or more amino, hydroxy, carboxy, halogen, nitro, cyano, alkoxy, aminocarbonyl, $C_{1-4}$alkoxycarbonyl, $C_{1-4}$alkoxycarbonylamino, sulfo, hydroxysulfonyloxy, dihydroxyphosphinoyloxy, phosphono, sulfamino, aminosulfonyl, aminoacylamino or dialkoxyphosphinoyl; heteroaryl or a non-aromatic heterocyclic hydrocarbon radical, all of which are optionally substituted with one or more straight, branched and/or cyclic hydrocarbon radical, amino, hydroxy, carboxy, halogen, nitro, cyano, alkoxy, aminocarbonyl, $C_{1-4}$alkoxycarbonyl, $C_{1-4}$alkoxycarbonylamino, sulfo, hydroxysulfonyloxy, dihydroxyphosphinoyloxy, phosphono, sulfamino, aminosulfonyl, aminoacylamino or dialkoxyphosphinoyl or a group

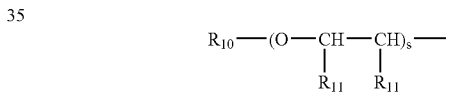

wherein s is an integer from 1 to 200; $R_{10}$ is hydrogen or an optionally substituted non-aromatic hydrocarbon radical; and $R_{11}$ is independently hydrogen or methyl; by a procedure substantially as disclosed in WO 02/43365.

The term "resistance" is intended to indicate a reduced sensitivity to a given treatment. Sensitivity can be defined in terms of IC$_{50}$, which indicates the amount or concentration of a given treatment or ionising radiation, which is lethal to 50% of the cells. An increase in IC$_{50}$ signifies a reduced sensitivity to a given therapy, and the cells are termed "resistant" if IC$_{50}$ increases by a factor of 10 or more, e.g. by a factor of 20-50. This definition is of particular relevance for in vitro studies, but of less relevance for in vivo studies, not to mention treatment of human beings. For in vivo studies and in human therapy a more feasible definition of resistance may be expressed as the overall failure of treatment, defined as progressing neoplastic diseases in a patient who previously responded to treatment. Progressing neoplastic diseases may be defined as >25% increase in the size of one or more lesions or the appearance of new lesions [*WHO Handbook for reporting results of cancer treatment*, Publication No. 48, Geneva, WHO, 1979].

The term "modulate" when used in relation to levels of activated NFκB means that the level of activated NFκB is increased or decreased compared to the level present in the absence of a compound of the general formula I. The level of activated NKκB is preferably decreased by the compound of formula I.

The term "apoptosis" is intended to indicate a genetically encoded cell death programme characterised by an "active decision" by the cell based on information from its environment, its own internal metabolism, its developmental history, etc to die. Unlike cells undergoing necrosis, cells stimulated to enter apoptosis are often capable of survival, but opt to die for the good of the whole organism. Apoptosis is also different from necrosis in that necrosis is often associated with traumatised tissue and cell bursts, whereas the cells condense in the course of apoptosis, and are degraded intracellularly in a controlled manner [Tran, *Science and Medicine*, 6, 18-27, 1999; Williams, *Trends Cell Biol.*, 2, 263-267, 1992].

PREFERRED EMBODIMENTS OF THE INVENTION

In a preferred embodiment, the invention relates to a compound of general formula II

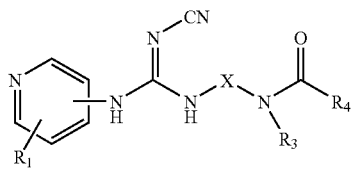

wherein $R_1$ and X are as indicated above, and N—C(=O)—$R_4$ together with the group $R_3$ in formula II form a 5-12 membered mono- or bicyclic ring system optionally including one or more additional heteroatoms selected from the group consisting of nitrogen, sulphur or oxygen, said ring system being optionally substituted with one or more substituents selected from the group consisting of halogen, hydroxy, cyano, nitro, alkoxy, alkoxycarbonyl, alkylcarbonyl, formyl, aminoalkyl, a straight or branched, saturated or unsaturated $C_{1-6}$ hydrocarbon radical, optionally substituted with halogen, hydroxy, cyano, nitro, alkoxy, alkoxycarbonyl, alkylcarbonyl, formyl or aminoalkyl, or —C(=O)$NR_5R_6$, —NHC(=O)$R_5$, —NHC(=O)$NR_5R_6$, —NHC(=O)$OR_5$, —OC(=O)$R_5$ or

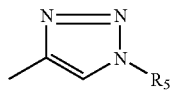

wherein $R_5$ and $R_6$ are the same or different and independently selected from the group consisting of hydrogen, $C_{1-6}$ alkyl optionally substituted with one or more halogen, hydroxy, cyano, nitro, amino, —NHC(=O)$NR_5R_6$, —NHC(=O)$OR_5$ or

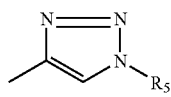

$R_1$ in formula I or II preferably represents hydrogen, halogen or one or more straight or branched, saturated or unsaturated $C_{1-6}$ hydrocarbon radical; and
X represents a straight or branched, saturated or unsaturated $C_{1-12}$ hydrocarbon diradical. $R_1$ is preferably hydrogen.

In a particularly preferred embodiment of the compound of formula I, $R_2$ and $R_3$ together with the nitrogen atom to which they are attached form a 5- or 6-membered aromatic or non-aromatic monocyclic ring system or a 9- or 10-membered aromatic or non-aromatic bicyclic ring system substituted with the group =O at a carbon atom thereof, and optionally substituted with halogen, hydroxy, alkoxy, alkoxycarbonyl, —C(=O)$NR_5R_6$, —NHC(=O)$NR_5R_6$ or NHC(=O)$R_5$, wherein $R_5$ and $R_6$ are independently hydrogen or $C_{1-6}$ alkyl optionally substituted with hydroxy, —NHC(=O)$NR_5R_6$ or

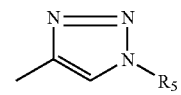

In a particularly preferred embodiment of the compound of formula II, —N—C(=O)—$R_4$ together with the group $R_3$ in formula II form a 5- or 6-membered aromatic or non-aromatic monocyclic ring system or a 9- or 10-membered aromatic or non-aromatic bicyclic ring system, optionally substituted with halogen, hydroxy, alkoxy, alkoxycarbonyl, —C(=O)$NR_5R_6$ or NHC(=O)$R_5$, wherein $R_5$ and $R_6$ are independently hydrogen or $C_{1-6}$ alkyl optionally substituted with hydroxy.

The monocyclic ring system is preferably pyridinone, piperidinone or pyrrolone.

The bicyclic ring system is preferably quinolone or indolone.

Said ring system may be substituted with hydrogen, halogen, —C(=O)$NR_5R_6$ or —NHC(=O)$NR_5R_6$, wherein $R_5$ is hydrogen and $R_6$ is $C_{1-4}$ alkyl optionally substituted with hydroxy or NHC(=O)$NR_5R_6$.

Examples of specific compounds of the invention are selected from the group consisting of
N-[6-(2-oxo-1,2-dihydro-1-quinolinyl)-1-hexyl]-N'-cyano-N"-(4-pyridyl)-guanidine (Compound 101),
N-[6-(6-chloro-2-oxo-1,2-dihydro-1-quinolinyl)-1-hexyl]-N'-cyano-N"-(4-pyridyl)-guanidine (Compound 102),
N-[6-(2-oxo-1,2,3,4-tetrahydro-1-quinolinyl)-1-hexyl]-N'-cyano-N"-(4-pyridyl)-guanidine (Compound 103),
N-[6-(2-oxo-1,2-dihydro-1-pyridyl)-1-hexyl]-N'-cyano-N"-(4-pyridyl)-guanidine (Compound 104),
N-[6-(4-(2-hydroxy-1-ethylcarbamoyl)-2-oxo-1,2-dihydro-1-quinolinyl)-hexyl]-N cyano-N"-(4-pyridyl)-guanidine (Compound 105),
N-[6-(5-(2-hydroxy-1-ethylcarbamoyl)-2-oxo-1,2-dihydro-1-pyridyl)-1-hexyl]-N'-cyano-N"-(4-pyridyl)-guanidine (Compound 106),
N-[6-(6-(2-hydroxy-1-ethylcarbamoyl)-2-oxo-1,2-dihydro-1-quinolinyl)-1-hexyl]-N cyano-N"-(4-pyridyl)-guanidine (Compound 107), and
N-[6-(6-(3-(N,N-dimethylamino)-1-propylcarbamoyl)-2-oxo-1,2-dihydro-1-quinolinyl)-1-hexyl]-N'-cyano-N"-(4-pyridyl)-guanidine (Compound 108).

General Methods of Preparation

Compounds of formula I may be prepared by reacting a compound of formula III wherein $R_1$ is as indicated for compounds of formula I, with a compound of formula IV, wherein X, $R_2$ and $R_3$ are as indicated for compounds of formula I, cf the reaction scheme shown below.

The reaction may be performed in a suitable solvent, such as pyridine, optionally in the presence of a tertiary amine, such as triethylamine, and a catalyst, such as 4-(N,N-dimethylamino)-pyridine and at temperatures between room temperature and 100° C. During the reaction $R_1$, X, $R_2$ and $R_3$ may temporarily contain suitable protection groups. The compounds of formulae III and IV are known from the literature or may be prepared by methods well known to persons skilled in the art.

In another embodiment a thiourea of the formula V in which the substituents are as defined above in (I), and if necessary temporarily protected, is reacted with one or more equivalents of N,N'-dicyclohexylcarbodiimide (DCCD) and of cyanamide in an inert solvent, such as acetonitrile, at or above room temperature, yielding a compound of formula I, see scheme. The compounds of formula V may be prepared by methods well known to persons skilled in the art.

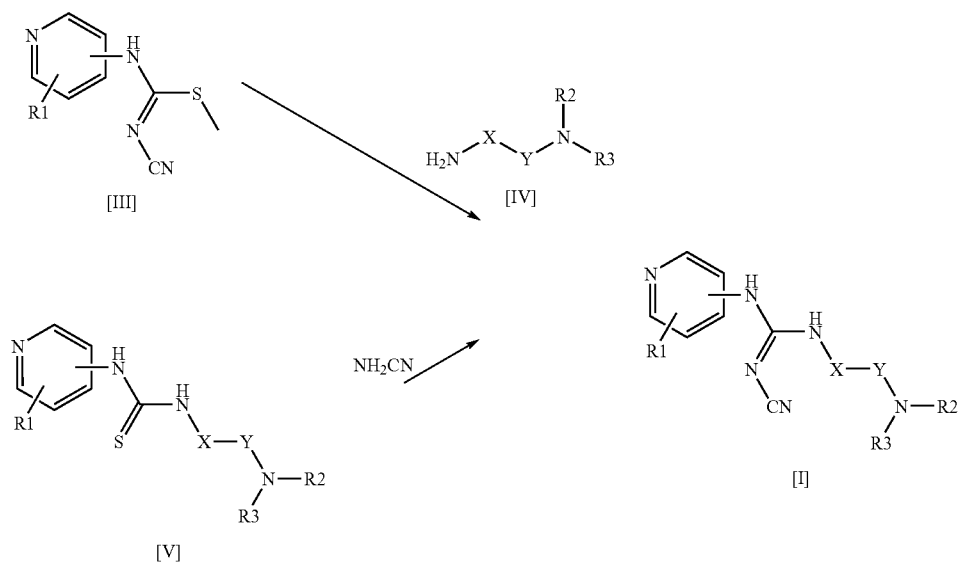

Pharmaceutical Formulations

In another aspect, the invention relates to a pharmaceutical composition comprising a compound of formula I. The composition of the present invention, both for veterinary and for human medical use, further comprises one or more pharmaceutically acceptable excipients or vehicles and optionally one or more other therapeutic ingredients. The excipients must be "acceptable" in the sense of being compatible with the other ingredients of the formulations and not deleterious to the recipient thereof.

Conveniently, the compound of formula I comprises from 0.1-100% by weight of the composition. Conveniently, a unit dose of the present composition contains between 0.07 mg and 1 g of a compound of formula I.

By the term "unit dose" is meant a unitary, i.e. a single dose which is capable of being administered to a patient, and which may be readily handled and packed, remaining as a physically and chemically stable unit comprising the compound of formula I in admixture with solid or liquid pharmaceutical diluents or excipients.

For the present purpose, the composition may be in a form suitable for oral (including sustained or timed release), rectal, parenteral (including subcutaneous, intraperitoneal, intramuscular, intraarticular and intravenous), transdermal, ophthalmic, topical, nasal or buccal administration.

The composition may conveniently be prepared by any of the methods well known in the art of pharmacy, e.g as disclosed in Remington, *The Science and Practice of Pharmacy*, 20th ed., 2000. All methods include the step of bringing the compound of formula I into association with the vehicle, which comprises one or more excipients. In general, the composition is prepared by uniformly and intimately bringing the compound of formula I into association with a liquid carrier or a finely divided solid carrier or both, and then, if necessary, shaping the product into the desired formulation.

Compositions of the present invention suitable for oral administration may be in the form of discrete units, such as capsules, sachets, tablets or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropylmethylcellulose, hydroxypropylcellulose, carbomers and polyvinylpyrrolidone. The composition may also be administered in the form of a bolus, electuary or paste.

A tablet may be made by compressing or moulding the compound of formula I in admixture with one or more excipients. Compressed tablets may be prepared by compressing, in a suitable machine, the active ingredient(s) in a free-flowing form such as a powder or granules, optionally mixed by a binder, such as e.g. lactose, glucose, starch, gelatine, acacia gum, tragacanth gum, sodium alginate, carboxymethylcellulose, methylcellulose, hydroxypropylmethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent.

Compositions for rectal administration may be may in the form of suppositories in which the compound of formula I is admixed with low melting water soluble or insoluble solids such as cocoa butter, hydrogenated vegetable oils, polyethylene glycol or fatty acids esters of polyethylene glycols, while elixirs may be prepared using myristyl palmitate.

Compositions suitable for parenteral administration conveniently comprise a sterile oily or aqueous preparation of the active ingredients, which is preferably isotonic with the blood of the recipient, e.g. isotonic saline, isotonic glucose solution or buffer solution. The composition may be conveniently sterilised by for instance filtration through a bacteria retaining filter, addition of sterilising agent to the composition, irradiation of the composition or heating of the composition. Liposomal formulations as disclosed in e.g. *Encyclopedia of Pharmaceutical Technology*, vol. 9, 1994, may also be suitable for parenteral administration.

Alternatively, the compound of formula I may be presented as a sterile, solid preparation, e.g. a freeze-dried powder, which is readily dissolved in a sterile solvent immediately prior to use.

Transdermal formulations may be in the form of a plaster or a patch.

Compositions suitable ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in *Encyclopedia of Pharmaceutical Technology*, vol. 2, 1989, may also be used to present the active ingredient for ophthalmic administration.

Compositions suitable for topical or ophthalmic administration include liquid or semi-liquid preparations such as liniments, lotions, gels, applicants, oil-in-water or water-in-oil emulsions such as creams, ointments or pastes; or solutions or suspensions such as drops.

Compositions suitable for nasal or buccal administration include powder, self-propelling and spray formulations, such as aerosols and atomisers.

In addition to the aforementioned ingredients, compositions comprising a compound of formula I may include one or more additional ingredients such as diluents, buffers, flavouring agents, colourant, surface active agents, thickeners, preservatives, e.g. methyl hydroxybenzoate (including anti-oxidants), emulsifying agents and the like.

For systemic treatment using a compound of the present invention daily doses of from 0.001-500 mg per kilogram body weight, preferably from 0.002-100 mg/kg of mammal body weight, for example 0.003-20 mg/kg or 0.003 to 5 mg/kg of a compound of formula I is administered, typically corresponding to a daily dose for an adult human of from 0.01 to 37000 mg. However, the present invention also provides compounds and compositions intended for administration with longer intervals, e.g. once a week, once every three weeks or once a month. For topical treatment of dermatological disorders, ointments, creams or lotions containing from 0.1-750 mg/g, and preferably from 0.1-500 mg/g, for example 0.1-200 mg/g of a compound of formula I is administered. For topical use in ophthalmic ointments, drops or gels containing from 0.1-750 mg/g, and preferably from 0.1-500 mg/g, for example 0.1-200 mg/g of a compound of formula I is administered. The oral compositions are formulated, preferably as tablets, capsules, or drops, containing from 0.07-1000 mg, preferably from 0.1-500 mg, of a compound of formula I per unit dose.

It has been found that compounds of formula I are capable of modulating the activity of IκB kinase (abbreviated IKK in the following). By modulating the activity of IKK in the cells it is possible to control the level of activated NFκB in the cells. Such compounds are therefore considered useful in the treatment of proliferative diseases and other conditions believed to be affected by the level of activated NFκB, e.g. inflammation.

NFκB is a member of the ReI family of transcription factors, which are ubiquitous in animal cells. ReI proteins can form dimers, the most common of which is designated NFκB. NFκB is a p50/p65 heterodimer which can activate transcription of genes containing the appropriate κB binding site. In non-stimulated cells, NFκB is maintained in the cytoplasm by an interaction with NFκB inhibiting proteins, the IκBS. In response to cell stimulation by e.g. anti-proliferative drugs or ionising radiation an IκB kinase complex (IKK) is rapidly activated and phosphorylates two serine residues in the NFκB binding domain of IκB. The phosphorylated IκB is then degraded by a 26S proteasome whereas NFκB is spared from degradation and translocates into the nucleus [Wang, *Science*, 274, 784-787, 1996, Cusak, *Cancer Research*, 60, 2323-2330, 2000; Karin, *Immunology*, 12, 2000, 85-98]. NFκB is thus always present in the cell, but in an inactivated form in non-stimulated cells. After translocation into the nucleus NFκB induces inter alia the anti-apoptotic genes c-IAP1, c-IAP2, TRAF1, TRAF2, Bfl-1/A1, Bcl-$X_L$ and Mn-SOD [Patel, *Oncogene*, 19, 2000, 4159-4169], which bring about resistance in the cells to apoptosis. This effect is referred to as the anti-apoptotic effect of NFκB. Anti-proliferative drugs and ionising radiation thus induce resistance in the cells to the treatments, which render them ineffective. Accordingly, activated NFκB is a key factor in induced resistance in e.g. cancer cells to anti-proliferative drugs and/or to ionising radiation. This is further supported by the fact that constitutively activated NFκB is found in cells from resistant cancer tumours [Patel, *Oncogene*, 19, 4159-4169, 2000]. Regardless of reduced resistance to any treatment, a reduction of the level of activated NFκB in the cell, e.g. by controlling the activity of IKK, will reduce the expression levels of genes encoding for anti-apoptotic factors inducing apoptosis in the cells [Schwartz, *Surgical Oncology*, 8, 1999, 143-153].

The role of activated NFκB is not restricted to preventing apoptosis. NFκB is also a critical activator of genes involved in inflammation and immunity. Activated NFκB induces the gene coding for cyclooxygenase 2 (COX2), which catalyses the synthesis of pro-inflammatory prostaglandins. Furthermore, at later stages in an inflammatory episode, COX2 catalyses the synthesis of the anti-inflammatory cyclopentenone prostaglandins. COX2 is also known to have anti-viral effects, which suggests that NFκB may also be a target in the therapy of inflammatory and viral diseases [Rossi, *Nature*, 403, 2000, 103-108]. NFκB is also responsible for the transcriptional regulation of genes important for many other vital cellular processes. NFκB e.g. regulates genes encoding cytokines and growth factors, adhesion molecules, acute phase reactants, receptors and chemoattractants [Schwartz, *Surgical Oncology*, 8, 1999, 143.153]. This is further supported by Rossi in *Nature*, 403, 103-108, 2000 who discloses that another type of compound, namely cyclopentenone prostaglandins inhibits IκB kinase, and that this makes cyclopentenone prostaglandins potentially valuable in the treatment of cancers, inflammation and viral infections.

IκB is non-covalently bound to NFκB and masks its nuclear localisation signal, thereby preventing translocation into the nucleus. Various IκBs have been identified and e.g. IκBα and IκBP are expressed in most cells where they bind to p65 ReI proteins, i.e. NFκB. Different IκB are phosphorylated by different factors allowing activation of NFκB in response to different stimuli.

The IκB kinase complex consist of three subunits, namely IKKα, IKKβ and IKKγ, with a combined molecular weight of 900 kDa. IKKα and IKKβ both exhibit IκB kinase activity and phosphorylate IκB, whereas IKKγ is a regulatory subunit. IKKα is 85 kDa protein and IKKβ is a 87 kDa protein, and the two subunits show a large degree of homology. Whereas both IKKα and IKKβ are catalytically active, it has surprisingly been shown that only IKKβ is essential for IKK phosphorylation of IκB.

As indicated above, controlling the level of activated NFκB by controlling the activity of IKK may be useful as therapeutic intervention in the treatment of proliferative diseases, e.g. cancers and in particular resistant cancer forms (for a further explanation, see WO 02/094322). Controlling the activity of IKK may also be useful in the treatment of inflammatory or viral diseases. Controlling the activity of IKK may either be as a single agent therapy, or it may be part of a combination treatment with other treatments.

In a preferred embodiment, the invention provides pharmaceutical compositions comprising a compound of formula I in combination with one or more other pharmacologically active compounds used in the treatment of proliferative diseases. Examples of compounds used in the treatment of proliferative diseases which may be used together with compounds of the present invention include S-triazine derivatives such as altretamine; enzymes such as asparaginase; antibiotic agents such as bleomycin, dactinomycin, daunorubicin, doxorubicin, idarubicin, mitomycin, epirubicin and plicamycin; alkylating agents such as busulfan, carboplatin, carmustine, chlorambucil, cisplatin, cyclophosphamide, dacarbazine, ifosfamide, lomustine, mechlorethamine, melphalan, procarbazine and thiotepa; antimetabolites such as cladribine, cytarabine, floxuridine, fludarabine, fluorouracil, hydroxyurea, mercaptopurine, methotrexate, gemcitabin, pentostatin and thioguanine; antimitotic agents such as etoposide, paclitaxel, teniposide, vinblastine, vinorelbin and vincristine; hormonal agents, e.g. aromatase inhibitors such as aminoglutethimide, corticosteroids, such as dexamethasone and prednisone, and luteinizing hormone releasing hormone (LH-RH); antiestrogens such as tamoxifen, formestan and letrozol; antiandrogens such as flutamide; and angiogenesis inhibitors. Finally, ionising radiation, although not readily defined as a compound, is heavily depended on in the treatment of neoplastic diseases, and may be combined with the compounds of the present invention. Due to the severe side effects often experienced by patients receiving anti-neoplastic treatment it is often desirable also to administer therapeutic agents which are not themselves anti-neoplastic, but rather help relieving the side effects. Such compounds include amifostin, leucovorin and mesna.

In particular, anti-proliferative compounds, such as paclitaxel, fluorouracil, etoposide, cyclophospamide, cisplatin, carboplatin, vincristine, gemcitabine, vinorelbine, chlorambucil, doxorubicin and melphalan appear beneficial in the combination compositions of the present invention.

It is envisaged that the combination composition of the present invention may be provided as mixtures of the compounds or as individual compounds intended for simultaneous or sequential administration. It lies within the capabilities of a skilled physician or veterinarian to decide time intervals in a sequential administration regime.

In particular, proliferative diseases or conditions to be treated by the present method include a variety of cancers and neoplastic diseases or conditions including leukaemia, acute myeloid leukaemia, chronic myeloid leukaemia, chronic lymphatic leukaemia, myelodysplasia, multiple myeloma, Hodgkin's disease or non-Hodgkin's lymphoma, small or non-small cell lung carcinoma, gastric, intestinal or colorectal cancer, prostate, ovarian or breast cancer, head, brain or neck cancer, cancer in the urinary tract, kidney or bladder cancer, malignant melanoma, liver cancer, uterine or pancreatic cancer.

The invention also relates to the use of compounds of formula I, optionally together with other anti-neoplastic compounds, as indicated above, in the manufacture of medicaments. In particular, said medicament is intended to be used for the treatment of proliferative diseases, e.g. cancers as mentioned above.

The invention is further described in the following examples which are not in any way intended to limit the scope of the invention as claimed.

METHODS OF PREPARATION

For $^1$H nuclear magnetic resonance (NMR) spectra (300 MHz) and $^{13}$C NMR (75.6 MHz) chemical shift values are quoted relative to internal tetramethylsilane (δ=0.00) or chloroform (δ=7.25) or deuteriochloroform (δ=76.81 for $^{13}$C NMR) standards. The value of a multiplet, either defined (singlet (s), doublet (d), triplet (t), quartet (q)) or not (broad (br)), at the approximate midpoint is given unless a range is quoted. The organic solvents used were anhydrous.

Preparation 1

1-[6-(N-tert-Butoxycarbonylamino)-1-hexyl]-1,2-dihydroquinoline-2-one

2-Hydroxyquinoline (640 mg) was added to a suspension of 600% sodium hydride (205 mg) in N,N-dimethylformamide (15 ml) and the mixture was stirred at 60° C. for 30 minutes. After cooling in ice a solution of N-(tert-butoxycarbonyl)-6-bromo-hexylamine (1.25 g) (Helv. Chim. Acta 76 891 (1993)) in N,N-dimethylformamide (10 ml) was added dropwise and stirring was continued overnight at room temperature. Ice and water were added and the mixture was extracted three times with ethyl acetate. The organic phases were washed with saturated sodium chloride, dried and evaporated to leave a yellow oil which after purification by chromatography on silica gel with ethyl acetate as eluent gave the desired compound as a colourless oil.

$^{13}$C NMR (DMSO) δ=160.8, 155.5, 139.2, 138.8, 130.7, 128.9, 121.7, 121.0, 120.2, 114.3, 77.2, 41.2, 29.3, 28.2, 27.0, 25.9

Preparation 2

1-(6-amino-1-hexyl)-1,2-dihydroquinoline-2-one

1-[6-(N-tert-Butoxycarbonylamino)-1-hexyl]-1,2-dihydroquinoline-2-one (480 mg) was treated with a large excess of hydrogen chloride in dietyl ether with stirring for 1 hour at room temperature. The crystalline product was isolated by filtration and redissolved in water whereafter the solution was made strongly alkaline with sodium hydroxide and extracted twice with chloroform. The organic phase was dried over potassium carbonate, filtered and evaporated to yield the title compound as a colourless oil.

$^{13}$C NMR (CDCl3) δ=162.1, 139.2, 139.0, 130.5, 129.0, 121.9, 121.8, 121.0, 114.2, 42.2, 42.0, 33.4, 27.5, 26.8, 26.6

Preparation 3

1-[6-(N-tert-Butoxycarbonylamino)-1-hexyl]-6-chloro-1,2-dihydroquinoline-2-one

Prepared as described in Preparation 1 but substituting 6-chloro-2-hydroxyquinoline for 2-hydroxyquinoline. Colourless crystals.

¹³C NMR (CDCl3) δ=161.7, 156.0, 137.8, 130.5, 128.0, 127.3, 123.1, 122.0, 115.6, 79.1, 42.3, 40.4, 30.0, 28.4, 27.4, 26.5, 26.4

Preparation 4

1-(6-amino-1-hexyl)-6-chloro-1,2-dihydroquinoline-2-one

Prepared as described in Preparation 2 but substituting 1-[6-(N-tert-Butoxycarbonylamino)-1-hexyl]-6-chloro-1,2-dihydroquinoline-2-one for 1-[6-(N-tert-Butoxycarbonylamino)-1-hexyl]-1,2-dihydroquinoline-2-one. Colourless crystals.
¹³C NMR (CDCl3) δ=161.7, 137.8, 130.5, 128.0, 127.3, 123.1, 122.0, 115.6, 42.4, 42.1, 33.6, 27.5, 26.8, 26.6

Preparation 5

1-[6-(N-tert-Butoxycarbonylamino)-1-hexyl]-1,2,3,4-tetrahydroquinoline-2-one 0.5M Potassium bis-(trimethylsilyl)-amide in toluene (10 ml) was added dropwise at −30° C. in an argon atmosphere to a stirred solution of 2-oxo-1,2,3,4-tetrahydroquinoline (735 mg) in tetrahydrofuran (50 ml). After further cooling to −50° C. a solution of N-(tert-butoxycarbonyl)-6-bromo-hexylamine (1.5 g) in tetrahydrofuran (10 ml) was added slowly. Subsequently the temperature was allowed to raise to room temperature followed by heating at 50-60° C. for 48 hours. Ice and water were added and the mixture was extracted twice with ethyl acetate. The organic phases were washed with saturated sodium chloride, dried and evaporated to leave a yellow oil which after purification by chromatography on silica gel with ethyl acetate/hexane (1:1) as eluent gave the desired compound as a colourless oil.
¹³C NMR (CDCl3) δ=170.1, 156.0, 139.6, 128.0, 127.4, 126.6, 122.7, 114.8, 79.1, 42.0, 40.6, 31.9, 30.0, 28.4, 27.1, 26.6, 26.5, 25.6

Preparation 6

1-(6-amino-1-hexyl)-1,2,3,4-tetrahydroquinoline-2-one

Prepared as described in Preparation 2 but substituting 1-[6-(N-tert-Butoxycarbonylamino)-1-hexyl]-1,2,3,4-tetrahydroquinoline-2-one for 1-[6-(N-tert-Butoxycarbonylamino)-1-hexyl]-1,2-dihydroquinoline-2-one. Colourless oil.
¹³C NMR (CDCl3) δ=170.2, 139.6, 128.0, 127.4, 126.6, 122.7, 114.8, 42.0, 33.6, 31.9, 27.2, 26.7, 26.6, 25.6

Preparation 7

1-[6-(N-tert-Butoxycarbonylamino)-1-hexyl]-1,2-dihydropyridine-2-one

Prepared as described in Preparation 1 but substituting 2-hydroxypyridine for 2-hydroxyquinoline. Yellow oil.
¹³C NMR (CDCl3) δ=162.6, 156.0, 139.2, 137.5, 121.2, 105.9, 79.0, 49.7, 40.4, 29.9, 29.2, 28.4, 26.3, 26.3

Preparation 8

1-(6-amino-1-hexyl)-1,2-dihydropyridine-2-one

Prepared as described in Preparation 2 but substituting 1-[6-(N-tert-Butoxycarbonylamino)-1-hexyl]-1,2-dihydropyridine-2-one for 1-[6-(N-tert-Butoxycarbonylamino)-1-hexyl]-1,2-dihydroquinoline-2-one. Colourless oil which was used in the next step without further purification.

Preparation 9

4-Methoxycarbonyl-2-hydroxyquinoline

2-Hydroxyquinoline-4-carboxylic acid (180 mg) was added to methanol saturated with HCl (10 ml). After stirring at room temperature overnight the title compound was isolated by filtration as colourless crystals.
¹³C NMR (DMSO) δ=165.4, 160.7, 139.9, 139.3, 131.0, 125.8, 123.9, 122.3, 115.8, 115.3, 52.8

Preparation 10

4-(2-hydroxy-1-ethylcarbamoyl)-2-hydroxyquinoline

A solution of 4-methoxycarbonyl-2-hydroxyquinoline (40 mg) and ethanolamine (0.1 ml) in chloroform (5 ml) was stirred at 60° C. for 48 hours. After cooling the colourless product was isolated by filtration.
¹³C NMR (DMSO) δ=165.8, 161.2, 146.3, 139.1, 130.6, 125.9, 121.9, 119.6, 116.1, 115.5, 59.5, 41.8

Preparation 11

1-[6-(N-tert-Butoxycarbonylamino)-1-hexyl]-4-[2-hydroxy-1-ethylcarbamoyl]-1,2-dihydroquinoline-2-one A mixture of 4-(2-hydroxy-1-ethylcarbamoyl)-2-hydroxyquinoline (1.2 g), N-(tert-butoxycarbonyl)-6-bromo-hexylamine (2.2 g), cesium carbonate (4 g) and N,N-dimethylformamide (50 ml) was stirred for 6 hours at 60° C. followed by stirring overnight at room temperature. Ice and water were added and the mixture was extracted three times with ethyl acetate. The organic phases were washed with saturated sodium chloride, dried and evaporated to leave a yellow oil which after purification by chromatography on silica gel with ethyl acetate/methanol/aqueous ammonia (45:5:1.5) as eluent gave the desired compound as a light brown solid.
¹³C NMR (CDCl3) δ=167.0, 161.5, 156.1, 145.5, 139.1, 131.4, 127.6, 122.8, 119.1, 118.0, 114.5, 79.1, 61.6, 42.8, 42.2, 40.4, 29.8, 28.4, 27.2, 26.4, 26.3

Preparation 12

1-(6-Amino-1-hexyl)-4-[2-hydroxy-1-ethylcarbamoyl]-1,2-dihydroquinoline-2-one

Prepared as described in Preparation 2 but substituting 1-[6-(N-tert-butoxy-carbonylamino)-1-hexyl]-4-[2-hydroxy-1-ethylcarbamoyl]-1,2-dihydro-quinoline-2-one for 1-[6-(N-tert-Butoxycarbonylamino)-1-hexyl]-1,2-dihydroquinoline-2-one. Colourless solid which was used in the next step without further purification.

Preparation 13

5-(2-hydroxy-1-ethylcarbamoyl)-2-hydroxypyridine

A mixture of 6-hydroxynicotinic acid (1.4 g), thionylchloride (1.1 ml) and dichloromethane (25 ml) was refluxed for 2 hours to form a clear solution. After evaporation the residue was evaporated twice from toluene, redissolved in dichloromethane with stirring and cooled in ice. A solution of ethanolamine (5 ml) in dichloromethane (20 ml) was added dropwise during 30 minutes followed by stirring for 2 hours at room temperature. Water was added and after extraction three times with dichloromethane, the aqueous phase was freeze-dried. The crude product was purified by chromatography on silica gel with ethyl acetate/methanol/aqueous ammonia as eluent. Fractions containing the title compound were evaporated and the product crystallised from acetone.

$^1$H NMR (DMSO) δ=11.80 (bs, OH), 8.20 (t, NH), 7.99 (d, 1H), 7.86 (dd, 1H), 6.34 (d, 1H), 4.70 (bs, OH), 3.47 (t, 2H), 3.26 (q, 2H)

Preparation 14

1-[6-(N-tert-Butoxycarbonylamino)-1-hexyl]-5-[2-hydroxy-1-ethylcarbamoyl]-1,2-dihydropyridine-2-one Prepared as described in Preparation 11 but substituting 5-(2-hydroxy-1-ethylcarbamoyl)-2-hydroxypyridine for 4-(2-hydroxy-1-ethylcarbamoyl)-2-hydroxyquinoline. Yellow solid.

$^{13}$C NMR (CDCl3) δ=164.9, 162.4, 156.3, 140.7, 136.9, 119.6, 113.4, 79.3, 62.0, 50.3, 42.8, 40.3, 29.8, 29.0, 28.5, 26.1, 26.0

Preparation 15

1-(6-amino-1-hexyl)-5-[2-hydroxy-1-ethylcarbamoyl]-1,2-dihydropyridine-2-one

Prepared as described in Preparation 2 but substituting 1-[6-(N-tert-butoxycarbonylamino)-1-hexyl]-5-[2-hydroxy-1-ethylcarbamoyl]-1,2-dihydropyridine-2-one for 1-[6-(N-tert-Butoxycarbonylamino)-1-hexyl]-1,2-dihydroquinoline-2-one.

Preparation 16

6-(2-hydroxy-1-ethylcarbamoyl)-2-hydroxyquinoline

A mixture of 6-carboxy-2-hydroxyquinoline (3.6 g), thionylchloride (25 ml), three drops of N,N-dimethylformamide and dichloromethane (25 ml) was heated slowly during 45 minutes until a clear solution was formed. After evaporation the residue was evaporated twice from toluene, redissolved in dichloromethane with stirring and cooled in ice. A solution of ethanolamine (10 ml) in dichloromethane (20 ml) was added dropwise during 30 minutes while a yellow oil separated. After stirring for 2 hours at room temperature and evaporation in vacuo the residue was stirred with ethyl acetate and methanol and the title compound was isolated by filtration and washed with methanol.

$^{13}$C NMR (DMSO) δ=165.5, 161.9, 140.5, 140.3, 129.0, 127.9, 127.3, 122.5, 118.3, 114.7, 59.7, 42.1

Preparation 17

1-[6-(N-tert-Butoxycarbonylamino)-1-hexyl]-6-[2-hydroxy-1-ethylcarbamoyl]-1,2-dihydroquinoline-2-one Prepared as described in Preparation 11 but substituting 6-(2-hydroxy-1-ethylcarbamoyl)-2-hydroxyquinoline for 4-(2-hydroxy-1-ethylcarbamoyl)-2-hydroxyquinoline.

$^{13}$C NMR (CDCl3) δ=167.1, 162.0, 156.1, 141.2, 139.0, 129.1, 128.3, 127.8, 122.6, 120.5, 114.2, 79.2, 62.2, 42.9, 42.4, 40.5, 29.9, 28.5, 27.4, 26.5, 26.4

Preparation 18

1-(6-amino-1-hexyl)-6-[2-hydroxy-1-ethylcarbamoyl]-1,2-dihydroquinoline-2-one

Prepared as described in Preparation 2 but substituting 1-[6-(N-tert-butoxycarbo-nylamino)-1-hexyl]-6-[2-hydroxy-1-ethylcarbamoyl]-1,2-dihydroquinoline-2-one for 1-[6-(N-tert-Butoxycarbonylamino)-1-hexyl]-1,2-dihydroquinoline-2-one.

Preparation 19

6-[3-(N,N-dimethylamino)-1-propylcarbamoyl]-2-hydroxyquinoline

Prepared as described in Preparation 16 but substituting 3-(N,N-dimethylamino)-1-propylamine for ethanolamine. The crude product was purified by chromatography on silica gel with ethyl acetate/methanol/aqueous ammonia (80:20:5) as eluent followed by crystallisation from acetone.

$^{13}$C NMR (DMSO) δ=165.3, 162.0, 140.6, 140.4, 129.0, 128.1, 127.3, 122.6, 118.4, 114.9, 57.0, 45.2, 37.8, 27.1

Preparation 20

1-[6-(N-tert-Butoxycarbonylamino)-1-hexyl]-6-[3-(N,N-dimethylamino)-1-propylcarbamoyl]-1,2-dihydroquinoline-2-one Prepared as described in Preparation 11 but substituting 6-[3-(N,N-dimethyl-amino)-1-propylcarbamoyl]-2-hydroxyquinoline for 4-(2-hydroxy-1-ethyl-carbamoyl)-2-hydroxyquinoline.

$^{13}$C NMR (CDCl3) δ=165.9, 162.1, 156.0, 141.1, 139.2, 128.9, 128.3, 128.2, 122.5, 120.5, 114.1, 79.1, 58.8, 45.1, 42.4, 40.5, 40.1, 30.0, 28.5, 27.5, 26.6, 26.5, 24.9

Preparation 21

1-(6-amino-1-hexyl)-6-[3-(N,N-dimethylamino)-1-propylcarbamoyl]-1,2-dihydroquinoline-2-one Prepared as described in Preparation 2 but substituting 1-[6-(N-tert-butoxy-carbonylamino)-1-hexyl]-6-[3-(N,N-dimethylamino)-1-propylcarbamoyl]-1,2-dihydroquinoline-2-one for 1-[6-(N-tert-Butoxycarbonylamino)-1-hexyl]-1,2-dihydroquinoline-2-one.

Example 1

N-[6-(2-oxo-1,2-dihydro-1-quinolinyl)-1-hexyl]-N'-cyano-N''-(4-pyridyl)-guanidine (Compound 101)

A mixture of 1-(6-amino-1-hexyl)-1,2-dihydroquinoline-2-one (320 mg), S-methyl-N-cyano-N'-4-pyridyl-isothiourea (210 mg), triethylamine (0.31 ml), 4-(N,N-dimethylamino)-pyridine (7 mg) and pyridine (10 ml) was stirred overnight at 60° C. After cooling to room temperature the pyridine was removed by evaporation twice with toluene in vacuo and the residue was distributed between water and ethyl acetate. The organic phase was dried and evaporated to yield a crude product which was purified by chromatography on silica gel with ethyl acetate/methanol/aqueous ammonia (40:10:1.25) as eluent. The pure fractions were pooled, evaporated, triturated with ethyl acetate and dried in vacuo to give the title compound.

$^{13}$C NMR (DMSO) δ=160.8, 157.1, 150.0, 145.8, 139.2, 138.7, 130.7, 128.9, 121.7, 121.0, 120.3, 116.4, 114.5, 114.4, 41.7, 41.2, 30.6, 28.5, 27.0, 25.9

Example 2

N-[6-(6-chloro-2-oxo-1,2-dihydro-1-quinolinyl)-1-hexyl]-N-cyano-N"-(4-pyridyl)-guanidine (Compound 102)

Prepared as described in Example 1 but substituting 1-(6-amino-1-hexyl)-6-chloro-1,2-dihydroquinoline-2-one for 1-(6-amino-1-hexyl)-1,2-dihydroquinoline-2-one. Yellow solid.

$^{13}$C NMR (DMSO) δ=160.6, 157.1, 150.0, 145.8, 138.2, 137.5, 130.3, 127.8, 125.8, 122.3, 121.5, 116.5, 116.4, 114.5, 41.6, 41.4, 28.5, 27.0, 25.8

Example 3

N-[6-(2-oxo-1,2,3,4-tetrahydro-1-quinolinyl)-1-hexyl]-N'-cyano-N"-(4-pyridyl)-guanidine (Compound 103)

Prepared as described in Example 1 but substituting 1-(6-amino-1-hexyl)-1,2,3,4-tetrahydroquinoline-2-one for 1-(6-amino-1-hexyl)-1,2-dihydroquinoline-2-one. Colourless crystals.

$^{13}$C NMR (DMSO) δ=169.0, 157.2, 149.9, 145.9, 139.1, 127.8, 127.2, 126.3, 122.2, 116.4, 114.7, 114.5, 41.6, 40.8, 31.3, 28.5, 26.6, 25.8, 24.7

Example 4

N-[6-(2-oxo-1,2-dihydro-1-pyridyl)-1-hexyl]-N'-cyano-N"-(4-pyridyl)-guanidine (Compound 104)

Prepared as described in Example 1 but substituting 1-(6-amino-1-hexyl)-1,2-dihydropyridine-2-one for 1-(6-amino-1-hexyl)-1,2-dihydroquinoline-2-one. Colourless solid.

$^{1}$H NMR (DMSO) δ=9.32 (bs, 1H), 8.39 (bd, 2H), 7.81 (bt, 1H), 7.65 (dd, 1H), 7.37 (m, 1H), 7.22 (bd, 2H), 6.35 (bd, 1H), 6.19 (dt, 1H), 3.85 (t, 2H), 3.25 (q, 2H), 1.62 (m, 2H), 1.52 (m, 2H), 1.4-1.2 (m, 4H)

Example 5

N-[6-(4-(2-hydroxy-1-ethylcarbamoyl)-2-oxo-1,2-dihydro-1-quinolinyl)-1-hexyl]-N'-cyano-N"-(4-pyridyl)-guanidine (Compound 105)

Prepared as described in Example 1 but substituting 1-(6-amino-1-hexyl)-4-[2-hydroxy-1-ethylcarbamoyl]-1,2-dihydroquinoline-2-one for 1-(6-amino-1-hexyl)-1,2-dihydroquinoline-2-one.

$^{13}$C NMR (DMSO) δ=165.7, 160.3, 157.1, 150.0, 145.8, 145.3, 138.9, 131.1, 126.8, 121.9, 118.7, 117.3, 116.4, 114.9, 114.5, 59.5, 41.8, 41.6, 41.3, 28.5, 27.0, 25.8

Example 6

N-[6-(5-(2-hydroxy-1-ethylcarbamoyl)-2-oxo-1,2-dihydro-1-pyridyl)-1-hexyl]-N'-cyano-N"-(4-pyridyl)-guanidine (Compound 106)

Prepared as described in Example 1 but substituting 1-(6-amino-1-hexyl)-5-[2-hydroxy-1-ethylcarbamoyl]-1,2-dihydropyridine-2-one for 1-(6-amino-1-hexyl)-1,2-dihydroquinoline-2-one.

$^{1}$H NMR (DMSO) δ=8.37 (m, 2H), 8.32 (d, 1H), 8.3-7.7 (bs, 1H), 8.21 (t, 1H), 7.84 (dd, 1H), 7.20 (bd, 2H), 6.39 (d, 1H), 3.91 (t, 2H), 3.48 (t, 2H), 3.34-3.20 (m, 5H), 1.65 (m, 2H), 1.53 (m, 2H), 1.43-1.21 (m, 4H)

Example 7

N-[6-(6-(2-hydroxy-1-ethylcarbamoyl)-2-oxo-1,2-dihydro-1-quinolinyl)-1-hexyl]-N'-cyano-N"-(4-pyridyl)-guanidine (Compound 107)

Prepared as described in Example 1 but substituting 1-(6-amino-1-hexyl)-6-[2-hydroxy-1-ethylcarbamoyl]-1,2-dihydroquinoline-2-one for 1-(6-amino-1-hexyl)-1,2-dihydroquinoline-2-one.

$^{13}$C NMR (DMSO) δ=165.3, 160.9, 157.1, 150.1, 145.8, 140.4, 139.5, 129.3, 128.3, 127.8, 121.6, 119.6, 116.4, 114.5, 114.3, 59.7, 42.1, 41.6, 41.4, 28.5, 27.0, 25.8

Example 8

N-[6-(6-(3-(N,N-dimethylamino)-1-propylcarbamoyl))-2-oxo-1,2-dihydro-1-quinolinyl)-1-hexyl]-N-cyano-N"-(4-pyridyl)-guanidine (Compound 108)

Prepared as described in Example 1 but substituting 1-(6-amino-1-hexyl)-6-[3-(N,N-dimethylamino)-1-propylcarbamoyl]-1,2-dihydroquinoline-2-one for 1-(6-amino-1-hexyl)-1,2-dihydroquinoline-2-one.

$^{13}$C NMR (DMSO) δ=165.1, 161.0, 157.4, 149.9, 146.1, 140.5, 139.6, 129.3, 128.3, 128.0, 121.7, 119.7, 116.5, 114.6, 114.4, 57.0, 45.2, 41.7, 41.5, 37.8, 28.6, 27.1, 25.9

The invention claimed is:
1. A compound of formula I

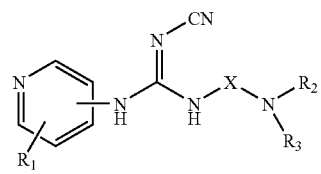

wherein
$R_1$ is one or more same or different substituents independently selected from the group consisting of hydrogen, halogen or a straight or branched, saturated or unsaturated $C_{1-6}$ hydrocarbon radical, optionally substituted with halogen, hydroxy, cyano, nitro, carboxy, alkoxy, alkoxycarbonyl, alkylcarbonyl, formyl, amino, aminoalkyl, aminocarbonyl, alkylcarbonylamino, sulfo, aminosulfonyl, alkylsulfonylamino, hydroxysulfonyloxy, dihydroxyphosphinoyloxy or phosphono;
X is a straight or branched, saturated or unsaturated $C_{1-12}$ hydrocarbon diradical, optionally substituted with halogen, hydroxy, cyano, nitro, carboxy, alkoxy, alkoxycarbonyl, alkylcarbonyl, formyl, amino, aminoalkyl, aminocarbonyl, alkylcarbonylamino, sulfo, aminosulfonyl, alkylsulfonylamino, hydroxysulfonyloxy, dihydroxyphosphinoyloxy or phosphono; and $R_2$ and $R_3$ together with the nitrogen atom to which they are attached form a 5-12 membered monocyclic ring system or an unsaturated or partially saturated quinoline or indole ring system optionally including one or more additional heteroatoms selected from the group consisting of nitrogen, sulphur or oxygen, said ring system being substituted with a group =O at one carbon atom thereof, and optionally substituted with one or more substituents selected from the group consisting of halogen, hydroxy, cyano, nitro, alkoxy, alkoxycarbonyl, alkylcarbonyl, formyl, aminoalkyl, a straight or branched, saturated or unsaturated $C_{1-6}$ hydrocarbon radical, optionally substituted with halogen, hydroxy, cyano, nitro, alkoxy, alkoxycarbonyl, alkylcarbonyl, formyl or aminoalkyl, or —C(=O)NR$_5$R$_6$, —NHC(=O)R$_5$, —NHC(=O)R$_5$R$_6$, —NHC(=O)OR$_5$, —OC(=O)R$_5$ or

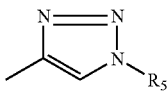

wherein $R_5$ and $R_6$ are the same or different and independently selected from the group consisting of hydrogen, $C_{1-6}$ alkyl optionally substituted with one or more halogen, hydroxy, cyano, nitro, amino, —NHC(=O)R$_5$R$_6$, —NHC(=O)OR$_5$ or

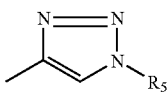

provided that $R_1$ is not attached to the nitrogen atom of the pyridyl ring;

or a pharmaceutically acceptable salt or N-oxide thereof.

2. A compound according to claim 1 of formula II

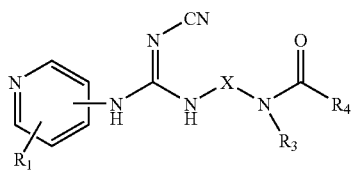

wherein $R_1$ and X are as indicated in claim 1, and N—C(=O)—R$_4$ together with the group R$_3$ in formula II form a 5-12 membered monocyclic ring system or an unsaturated or partially saturated quinolone or an indolone ring system optionally including one or more additional heteroatoms selected from the group consisting of nitrogen, sulphur or oxygen, said ring system being optionally substituted with one or more substituents selected from the group consisting of halogen, hydroxy, cyano, nitro, alkoxy, alkoxycarbonyl, alkylcarbonyl, formyl, aminoalkyl, a straight or branched, saturated or unsaturated $C_{1-6}$ hydrocarbon radical, optionally substituted with halogen, hydroxy, cyano, nitro, alkoxy, alkoxycarbonyl, alkylcarbonyl, formyl or aminoalkyl, or —C(=O)NR$_5$R$_6$, —NHC(=O)R$_5$, —NHC(=O)R$_5$R$_6$, —NHC(=O)OR$_5$, —OC(=O)R$_5$ or

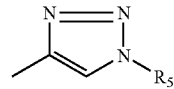

wherein $R_5$ and $R_6$ are the same or different and independently selected from the group consisting of hydrogen, $C_{1-6}$ alkyl optionally substituted with one or more halogen, hydroxy, cyano, nitro, amino, —NHC(=O)R$_5$R$_6$, —NHC(=O)OR$_5$ or

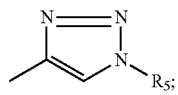

or a pharmaceutically acceptable salt or N-oxide thereof.

3. A compound according to claim 1, wherein $R_1$ is hydrogen, halogen or a straight or branched, saturated or unsaturated $C_{1-4}$ hydrocarbon radical; and X is a straight or branched, saturated or unsaturated $C_{4-10}$ hydrocarbon diradical; or a pharmaceutically acceptable salt or N-oxide thereof.

4. A compound according to claim 3, wherein $R_1$ is hydrogen; or a pharmaceutically acceptable salt or N-oxide thereof.

5. A compound according to claim 1, wherein $R_2$ and $R_3$ together with the nitrogen atom to which they are attached form a 5- or 6-membered aromatic or non-aromatic monocyclic ring system or an unsaturated or partially saturated quinoline or indole ring system substituted with the group =O at one carbon atom thereof, and optionally substituted with halogen, hydroxy, alkoxy, alkoxycarbonyl, —C(=O)NR$_5$R$_6$, —NHC(=O)R$_5$, —NHC(=O)R$_5$R$_6$ or

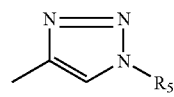

wherein $R_5$ and $R_6$ are independently hydrogen or $C_{1-6}$ alkyl optionally substituted with hydroxy, —NHC(=O)R$_5$R$_6$ or

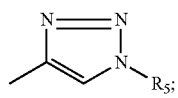

or a pharmaceutically acceptable salt or N-oxide thereof.

6. A compound according to claim 2, wherein N—C(=O)—R$_4$ together with the group R$_3$ in formula II form a 5- or 6-membered aromatic or non-aromatic monocyclic ring system or an unsaturated or partially saturated quinolone or an indolone ring system, optionally substituted with halogen, hydroxy, alkoxy, alkoxycarbonyl, —C(=O)NR$_5$R$_6$ or NHC(=O)R$_5$, wherein $R_5$ and $R_6$ are independently hydrogen or $C_{1-6}$ alkyl optionally substituted with hydroxyl; or a pharmaceutically acceptable salt or N-oxide thereof.

7. A compound according to claim 5 or 6, wherein the monocyclic ring system is pyridinone, piperidinone or pyrrolone; or a pharmaceutically acceptable salt or N-oxide thereof.

8. A compound according to claim 1, wherein the ring system is substituted with hydrogen, halogen, —C(=O)NR$_5$R$_6$, wherein R$_5$ is hydrogen and R$_6$ is C$_{1-4}$ alkyl optionally substituted with hydroxy or —NHC(=O)NR$_5$R$_6$; or a pharmaceutically acceptable salt or N-oxide thereof.

9. A compound according to claim 1 that is:
   N-[6-(2-oxo-1,2-dihydro-1-quinolinyl)-1-hexyl]-N'-cyano-N''-(4-pyridyl)-guanidine,
   N-[6-(6-chloro-2-oxo-1,2-dihydro-1-quinolinyl)-1-hexyl]-N'-cyano-N''-(4-pyridyl)-guanidine,
   N-[6-(2-oxo-1,2,3,4-tetrahydro-1-quinolinyl)-1-hexyl]-N'-cyano-N''-(4-pyridyl)-guanidine,
   N-[6-(2-oxo-1,2-dihydro-1-pyridyl)-1-hexyl]-N'-cyano-N''-(4-pyridyl)-guanidine,
   N-[6-(4-(2-hydroxy-1-ethylcarbamoyl)-2-oxo-1,2-dihydro-1-quinolinyl)-1-hexyl]-N'-cyano-N''-(4-pyridyl)-guanidine,
   N-[6-(5-(2-hydroxy-1-ethylcarbamoyl)-2-oxo-1,2-dihydro-1-pyridyl)-1-hexyl]-N'-cyano-N''-(4-pyridyl)-guanidine,
   N-[6-(6-(2-hydroxy-1-ethylcarbamoyl)-2-oxo-1,2-dihydro-1-quinolinyl)-1-hexyl]-N'-cyano-N''-(4-pyridyl)-guanidine,
   N-[6-(6-(3-(N,N-dimethylamino)-1-propylcarbamoyl)-2-oxo-1,2-dihydro-1-quinolinyl)-1-hexyl]-N'-cyano-N''-(4-pyridyl)-guanidine;
or a pharmaceutically acceptable salt or N-oxide thereof.

10. A pharmaceutical composition comprising a compound according to claim 1 or a pharmaceutically acceptable salt or N-oxide thereof, together with a pharmaceutically acceptable excipient or vehicle.

11. A composition according to claim 10, additionally comprising one or more other pharmacologically active compounds.

12. A composition according to claim 11, wherein said other pharmacologically active compound is an anti-neoplastic drug.

13. A method of treating a hyperproliferative or neoplastic disease, the method comprising administering to a patient in need thereof an effective amount of a compound according to claim 1.

14. The method of claim 13, wherein the hyperproliferative or neoplastic disease is leukaemia, acute myeloid leukaemia, chronic myeloid leukaemia, chronic lymphatic leukaemia, myelodysplasia, multiple myeloma, Hodgkin's disease or non-Hodgkin's lymphoma, small or non-small cell lung carcinoma, gastric, intestinal or colorectal cancer, prostate, ovarian or breast cancer, brain, head or neck cancer, urinary tract cancer, kidney or bladder cancer, malignant melanoma, liver cancer, uterine or pancreatic cancer.

15. The method of claim 13 or 14 further comprising administering one or more other pharmacologically active compounds.

16. The method of claim 15, wherein said other pharmacologically active compound is an anti-neoplastic drug.

17. The composition of claim 12, wherein the anti-neoplastic drug is paclitaxel, fluorouracil, etoposide, cyclophospamide, cisplatin, carboplatin, vincristine, gemcitabine, vinorelbine, chlorambucil, doxorubicin or melphalan.

18. The method of claim 16, wherein the anti-neoplastic drug is paclitaxel, fluorouracil, etoposide, cyclophospamide, cisplatin, carboplatin, vincristine, gemcitabine, vinorelbine, chlorambucil, doxorubicin or melphalan.

* * * * *